(12) United States Patent
Li et al.

(10) Patent No.: US 6,927,061 B2
(45) Date of Patent: Aug. 9, 2005

(54) HUMAN OVARIAN MESOTHELIAL CELLS AND METHODS OF ISOLATION AND USES THEREOF

(75) Inventors: Rong-hao Li, Millbrae, CA (US); Laura Bald, Los Altos, CA (US); Jennie Powell Mather, Millbrae, CA (US)

(73) Assignee: Raven Biotechnologies, Inc., South San Francisco, CA (US)

( * ) Notice: Subject to any disclaimer, the term of this patent is extended or adjusted under 35 U.S.C. 154(b) by 474 days.

(21) Appl. No.: 10/445,179

(22) Filed: May 23, 2003

(65) Prior Publication Data

US 2003/0207449 A1 Nov. 6, 2003

Related U.S. Application Data

(62) Division of application No. 09/545,659, filed on Apr. 10, 2000.

(51) Int. Cl.[7] .................................................. C12N 5/00
(52) U.S. Cl. ...................... 435/366; 435/325; 435/378
(58) Field of Search ................................ 435/366, 378, 435/325

(56) References Cited

U.S. PATENT DOCUMENTS

| | | | |
|---|---|---|---|
| 5,525,337 A | * | 6/1996 | Willingham et al. |
| 5,710,038 A | | 1/1998 | Mes-Masson et al. |
| 6,004,528 A | | 12/1999 | Bergstein |
| 6,083,502 A | * | 7/2000 | Pastan et al. |

FOREIGN PATENT DOCUMENTS

EP 0 911 389 4/1999

OTHER PUBLICATIONS

Auersperg et al., (1984). "Human ovarian surface epithelium in primary culture," In Vitro 20(10):743–755.
Barnes et al. (1980). "Methods for growth of cultured cells in serum–free medium," Anal. Biochem. 102:255–270.
Boring et al. (1991). "Cancer statistics, 1991" Ca–A Cancer Journal for Clinicians 41(1):19–36.
Buck et al. (1982). "Monoclonal antibodies specific for cell culture mycoplasmas," In Vitro 18(4):377–381.
Dubeau et al. (1990). "Culture of human fetal ovarian epithelium in a chemically–defined, serum–free medium: A model for ovarian carcinogenesis," Anticancer Research 10:1233–1240.
Freshney, R.I. (ed), (1987). Animal Cell Culture pp. vii–xii. (Table of Contents).
Ham et al. (1979). "Media and growth requirements," Meth. Enzy. 58:44–93.
Harlow et al. (eds), (1988). Antibodies, A Laboratory Manual pp. iii–ix. (Table of Contents).
Kohler et al. (1975) "Continuous cultures of fused cells secreting antibody of predefined specificity," Nature 256: 495–497.
Kruk et al. (1990). "A simplified method to culture human ovarian surface epithelium," Laboratory Investigation 63(1):132–136.
Lavranos et al. (1999). "Evidence for ovarian granulosa stem cells: Telomerase activity and localization of the telomerase ribonucleic acid component in bovine ovarian follicles," Biol. of Reproduction 61:358–366.
Mather et al., Eds. (1998). Introduction to Cell and Tissue Culture Plenum Press, New York pp. xi–xiv. (Table of Contents).
Nicosia et al. (1988). "Neoplasms of the ovarian mesothelium," in Pathology of Human Neoplasms, Chapter 8, pp. 435–486.
Piquette et al. (1990). "Isolation and characterization of rabbit ovarian surface epithelium, granulosa cells, and peritoneal mesothelium in primary culture," In Vitro Cell. Dev. Biol. 26:471–481.
Scully. (1977). "Ovarian tumors," Am. J. Pathol. 87(3):686–720.
Siemens et al. (1988). "Serial propagation of human ovarian surface epithelium in tissue culture," J. Cell. Physiol. 134:347–356.
Stephen et al. (1997) "Characterization of Cell Surface Proteins Using Antibodies Raised to Antigens from Pancreatic Cell Lins," Abstract 1905—presentation materials: 17 pages.
Telfer et al. (1988). "The number of clonal precursors of the follicular epithelium in the mouse ovary," J. Reprod. Fert. 84:105–110.
Van Niekerk et al. (1989) "Marker Profile of Mesothelial Cells Versus Ovarian Carcinoma Cells," Int. J. Cancer 43:1065–1071.
Zeihmet et al. (1996) "Human Peritoneal Mesothelial Cells Are More Potent Than Ovarian Cancer Cells in Producing Tumor Marker CA–125," Gynecologic Oncology 62:384–389.

* cited by examiner

Primary Examiner—Leon B. Lankford, Jr.
(74) Attorney, Agent, or Firm—Morrison & Foerster LLP

(57) ABSTRACT

The invention discloses a substantially pure population of human ovarian mesothelial cells and methods of isolating and culturing the ovarian mesothelial cells. By carefully manipulating the microenvironment of the ovarian mesothelial cells, multiple passages are attainable wherein the ovarian mesothelial cells are capable of becoming ovary surface epithelial cells or granulosa cells. In addition, several methods of use of human ovarian mesothelial cells are disclosed herein.

2 Claims, 5 Drawing Sheets

HUMAN OVARIAN MESOTHELIAL CELLS AND METHODS OF ISOLATION AND USES THEREOF

CROSS-REFERENCE TO RELATED APPLICATIONS

This application is a divisional of U.S. patent application Ser. No. 09/545,659, filed on Apr. 10, 2000, which is incorporated herein by reference in its entirety.

TECHNICAL FIELD

This invention is in the field of developmental biology and cell biology. Specifically, this invention relates to a population of ovarian mesothelial cells that are capable of differentiating into ovarian surface epithelial cells and granulosa cells, methods of isolating the ovarian mesothelial cells, characterization of ovarian mesothelial cells, and uses of the ovarian mesothelial cells.

BACKGROUND ART

Ovarian cancer is one of the most common causes of death due to cancer in women. Boring C. C. et. al. CA-Cancer J. Clin. 41,19–36, (1991). In about 80–90% of ovarian cancer cases, the ovarian surface epithelium is thought to be the tissue source in which the cancerous transformation occurs. Nicosia S. V. Pathology of Human Neoplasms. New York: Raven Press 435–486, (1988); Scully R. E. Am. J. Pathol. 87:686–720, (1977). The ovarian surface epithelium (OSE) is a single cell layer covering the surface of the ovary and is contiguous with coelomic mesothelium at the ovarian hilum. Dubeau L. et. al. Anticancer Research 10: 1233–1240, (1990). The OSE cells are thought to be derived from mesothelial cells covering the gonadal ridge. Mesothelial cells stromalize, migrate inside the ovary, and become granulosa cells. Granulosa cells, one of the major endocrine cell types in the ovary, first appear in a primordial follicle as a single layer of cells surrounding an oocyte during prenatal life. As each follicle becomes active, the oocyte begins to enlarge in size and granulosa cells begin to divide, increase in number, and secrete estrogen. As the follicle matures, granulosa cells stop dividing and the follicle is erupted to the oocyte in a process known as ovulation. After ovulation, the granulosa cells then differentiate into luteal cells of the developing corpus luteum from which progesterone is secreted.

The lack of human ovary tissue models makes efforts to confirm the ovarian surface epithelium as the source of cancerous growth difficult. Further, there is a lack of understanding about the development of ovarian surface epithelial cell during oogenesis and follicle formation because culturing conditions in which the OSE cells can be isolated and still retain their original characteristics are still being refined. The identification, isolation, and characterization of an ovarian precursor cell that can reliably differentiate into multiple types of cells, such as OSE cells and granulosa cells, may be important in the understanding of the biology of ovarian cells and why cancerous transformations occur like in ovarian cancer and perhaps how the transformations can be prevented. However, the ovarian precursor cells, like many precursor cells, are few in number and difficult to isolate. Once isolated, ovarian precursor cells are difficult to culture to the extent that they retain their precursor traits. It is postulated that there are precursors to granulosa cells and OSE cells, however, the work accomplished to date only isolates OSE cells and granulosa cells but not a common precursor to both types of cells.

There have been several reports of isolation and culturing methods of human OSE cells. Kruk P. A. et. al. Laboratory Investigation 63(1), 132–136, (1990); Siemens C. H. and Auersperg N. Journal of Cellular Physiology 134, 347–356, (1988); Auersperg N. et. al. In Vitro 20(10) 743–755, (1984). In these reports, human OSE cells that are isolated and cultured are already in terminally differentiated form. The isolation and characterization of OSE cells and granulosa cells in rabbits have also been reported. Piquette G. N. and Timms B. G. In Vitro Cell. Dev.Biol.26: 471–481, (1990). However, the OSE cells are already differentiated and therefore, make studying events related to early OSE development or early cancerous transformation during OSE development difficult. Some research progress has been accomplished toward identifying precursors to granulosa cells. The number of clonal precursors of granulosa cells in mouse ovary has been determined to be small in number (about five) based on a technique of random X-chromosome inactivation and the use of an X-linked alloenzyme variant of phosphoglycerate kinase-1 (PGK-1), a variant of a glycolytic enzyme. Telfer E. et. al. J. Reprod. Fert. 84,105–110, (1988). Other research related to ovarian granulosa stem cells demonstrate that granulosa cells, not oocytes, are the source of telomerase activity in the ovary and therefore, as the authors state, their results supports their hypothesis that granulosa cells arise from a population of stem cells. Lavranos T. C., et. al. Biol. of Reproduction 61, 358–366, (1999). One line of thought in ovarian precursor cell research advocates the use of fetal, not adult, ovaries as a source of cells because precursor cells in fetus would presumably have higher activity and be greater in number than in adults. To this end, fetal epithelial cells from a region of the ovary called rete ovarii have been described but these cells are not described as having pluripotent capacity to differentiate into any other types of ovarian mesothelial cells. Dubeau et. al. Anticancer Research 10: 1233–1240, (1990).

Accordingly, there exists a need for methods to identify, isolate, culture, and characterize ovarian mesothelial cells that have pluripotent capabilities. The invention described herein overcomes many of the aforementioned shortcomings and also provides related advantages.

DISCLOSURE OF THE INVENTION

This invention is related to the field of developmental and cell biology. In one aspect, the invention relates to a population of substantially pure human ovarian mesothelial cells that have the pluripotent capability to differentiate into ovarian surface epithelial cells and granulosa cells.

In another aspect of this invention, the invention relates to methods of isolating a population of substantially pure human ovarian mesothelial cells that have the pluripotent capability to differentiate into ovarian surface epithelial cells and granulosa cells.

In yet another aspect of this invention, the invention relates to methods of maintaining a population of substantially pure human ovarian mesothelial cells that have the pluripotent capability to differentiate into ovarian surface epithelial cells and granulosa cells and maintaining or culturing these ovarian mesothelial cells such that the cells retain their pluripotent capacity.

In still another aspect of this invention, the invention relates to methods of providing a source of immunogen, and the uses of a substantially pure population of ovarian mesothelial cells as an immunogen.

In still another aspect of this invention, the invention relates to methods of generating a human ovarian tissue model by introducing a substantially pure population of human ovarian mesothelial cells into a non-human, mammalian recipient.

In another aspect of this invention, the invention relates to methods of providing cell therapy whereby a substantially pure population of human ovarian mesothelial cells are introduced into a heterologous recipient in a location which can support the proliferation and growth of the ovarian cells.

In another aspect of this invention, the invention relates to methods of providing a source of ovarian mesothelial tissue-specific biological components for developing pharmaceutical drugs wherein a substantially pure population of human ovarian mesothelial cells is used as a source of ovarian mesothelial biological components in which one or more of these ovarian mesothelial biological components are the targets of the drugs that are being developed.

In another aspect of this invention, the invention relates to methods of providing a source of nucleic acids or proteins for bioassay development wherein a substantially pure population of human ovarian mesothelial cells is used as a source of nucleic acids or proteins and wherein these nucleic acids or proteins are used as one or more principal components in a bioassay or the development of a bioassay.

BRIEF DESCRIPTION OF THE DRAWINGS

FIG. 2A shows magnification at 100× and FIG. 2B shows magnification at 400×.

FIG. 3A shows staining of ovarian mesothelial cells for cytokeratin 19. FIG. 3B shows staining of ovarian mesothelial cells for cytokeratins 13 and 16. FIG. 3C shows staining of ovarian mesothelial cells for cytokeratins 10, 11, and 18. FIG. 3D shows staining of ovarian mesothelial cells for vimentin. FIG. 3E shows staining of ovarian mesothelial cells for ovarian mesothelial cell surface antigen recognized by monoclonal antibody 5C8.

FIGS. 4A, 4B, and 4C show the morphology of ovarian surface epithelial cells resembling cystic structures.

MODES FOR CARRYING OUT THE INVENTION

Figure 1:
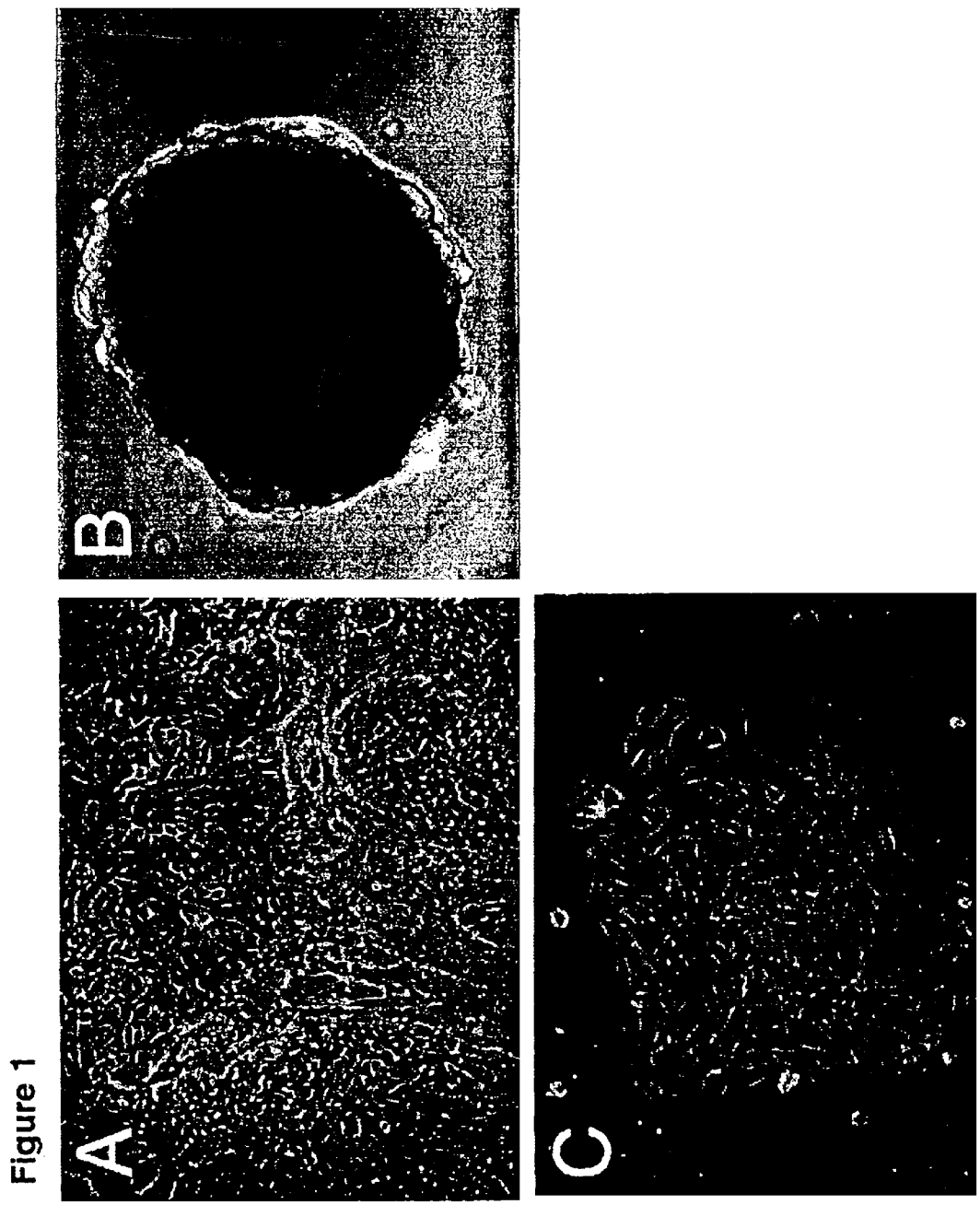
FIG. 1A is a microphotograph showing the outgrowth of human ovarian mesothelial cells from solid ovarian tissue.
FIG. 1B is a microphotograph showing the growth of human ovarian mesothelial cells as cell clusters in a suspension culture.
FIG. 1C is a microphotograph showing growth of human ovarian mesothelial cells as a monolayer.

The following detailed description of the invention is provided to aid those skilled in the art in practicing the present invention. This detailed description should not be construed to limit the present invention, as modifications of the embodiments disclosed herein may be made by those of ordinary skill in the art without departing from the spirit and scope of the present invention. Throughout this disclosure, various publications, patents, and published patent specifications are referenced by citation. The disclosure of these publications, patents, and published patents are hereby incorporated by reference in their entirety into the present disclosure.

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

As used in the specification and claims, the singular form "a", "an", and "the" include plural references unless the context clearly dictates otherwise. For example, the term "a cell" includes a plurality of cells, including mixtures thereof.

As used in the specification and claims, the terms "ovarian surface epithelial cells" and "OSE cells" are interchangeably and refer to "ovarian surface epithelial cells" and "OSE cells" of human origin.

"Ovarian mesothelial cells" refers to human cells derived from the mesoderm that have already committed to becoming cells of ovarian nature. More specifically, ovarian mesothelial cells of this invention refer to cells between the stage of being a mesothelial cell and the stage prior to becoming terminally differentiated to an ovarian surface epithelial cell or a granulosa cell. It is at this stage of being mesothelial cells and just prior to committing to being terminally differentiated ovarian mesothelial cell types that the ovarian mesothelial cells of this invention resides. The ovarian mesothelial cells of this invention have a pluripotent or multipotent capacity to become either ovarian surface epithelial cells or granulosa cells.

"Pluripotent" and "multipotent" are used interchangeably throughout and refer to a stage where a cell can still become one of a plurality of cells but can no longer become any type of cell in the body (i.e. no longer totipotent). "Pluripotent" cells are not referred to as "stem cells" but rather "progenitor cells" because they are progenitors to one or more type of a plurality of cells.

As used herein, "pre-determined ovarian" refers to a stage of development of a multipotent cell that is prior to the stage of being a primordial follicle and before the stage of terminally differentiated ovarian cells (such as granulosa cells or ovarian surface epithelial cells). Cells which are "pre-determined ovarian" are committed to becoming ovarian cells but have not begun to develop into terminally differentiated ovarian cells yet. Different factors cause pre-determined ovarian cells to begin differentiating. Non-limiting examples include exposure to serum, exposure to progesterone, estrogen, luteinizing hormone (LH), contact with surrounding tissue, microenvironment of the cells, and cell-cell contact with surrounding tissue.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins, and modifications of the immunoglobulin molecule that comprise an antigen recognition site of the required specificity.

The term "antigen" is a molecule which can include one or more epitopes to which an antibody can bind. An antigen is a substance which can have immunogenic properties, i.e., induce an immune response. Antigens are considered to be a type of immunogen. As used herein, the term "antigen" is intended to mean full length proteins as well as peptide fragments thereof containing or comprising one or a plurality of epitopes.

The terms "surface antigens" and "cell surface antigen" are used interchangeably herein and refer to the plasma membrane components of a cell. These component include, but are not limited to, integral and peripheral membrane proteins, glycoproteins, polysaccharides, lipids, and glycosylphosphatidylinositol (GPI)-linked proteins. An "integral membrane protein" is a transmembrane protein that extends across the lipid bilayer of the plasma membrane of a cell. A typical integral membrane protein consists of at least one membrane spanning segment that generally comprises hydrophobic amino acid residues. Peripheral membrane proteins do not extend into the hydrophobic interior of the lipid bilayer and they are bound to the membrane surface by noncovalent interaction with other membrane proteins. GPI-linked proteins are proteins which are held on the cell surface by a lipid tail which is inserted into the lipid bilayer.

The term "monoclonal antibody" as used herein refers to an antibody composition having a substantially homogeneous antibody population. It is not intended to be limited as regards to the source of the antibody or the manner in which it is made (e.g. by hybridoma or recombinant synthesis). Monoclonal antibodies are highly specific, being directed against a single antigenic site. In contrast to conventional (polyclonal) antibody preparations which typically include different antibodies directed against different determinants (epitopes), each monoclonal antibody is directed against a single determinant on the antigen.

"A population of monoclonal antibodies" refers to a plurality of heterogeneous monoclonal antibodies, i.e., individual monoclonal antibodies comprising the population may recognize antigenic determinants distinct from each other.

"Immunogen" refers to any substance that induces an immune response. A substance that is an immunogen is described as being "immunogenic". Induction of immune response includes but is not limited to activation of humoral responses (e.g. producing antibodies) or cellular responses (e.g. priming cytotoxic T cells), inflammatory responses (e.g. recruitment of leukocytes), and secretion of cytokines and lymphokines.

The term "heterologous" as applied to a cell used for immunization or transplantation means that the cell is derived from a genotypically distinct entity from the recipient. For example, a heterologous cell may be derived from a different species or a different individual from the same species as the recipient. An embryonic cell derived from an individual of one species is heterologous to an adult of the same species. "Heterologous" as applied to a recipient means that the recipient is a genotypically distinct entity from the source of the cells that are being introduced into the recipient.

"Explant" refers to ovarian tissues taken out of a human fetus. Generally, explants are used as a source of ovarian cells. Isolating the cells from the explant can be accomplished by several methods. One method is to place the ovarian tissue explant, either whole tissue or cut in smaller pieces, in a basal defining media and allow the ovarian cells to naturally migrate out of the solid tissue mass into the media. Another method is to subject the ovarian tissue to enzymatic digestion or to mechanical forces that forces cells away from the solid tissue.

A cell is of "ectodermal", "endodermal" or "mesodermal" origin, if the cell is derived, respectively, from one of the three germ layers—ectoderm, the endoderm, or the mesoderm of an embryo. The ectoderm is the outer layer that produces the cells of the epidermis, and the nervous system. The endoderm is the inner layer that produces the lining of the digestive tube and its associated organs. The middle layer, mesoderm, gives rise to several organs, including but not limited to heart, kidney, mesothelium, and gonads), connective tissues (e.g., bone, muscles, tendons), and the blood cells.

As used herein, a "substantially pure" population of ovarian mesothelial cells is a population of cells that is comprised at least about 85% ovarian mesothelial cells, preferably at least about 90%, and even more preferably at least about 95% or more.

The terms "medium", "cell culture medium", and "culture medium" are used interchangeably. The terms refer to the aqueous microenvironment in which the mammalian cells are grown in culture. The medium comprises the physicochemical, nutritional, and hormonal microenvironment.

A "defined medium," "basal cell-sustaining medium," "nutrient medium", and "basal nutrient medium" are used interchangeably herein and refer to a medium comprising nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: a) all essential amino acids, and usually the basic set of twenty amino acids plus cystine; b) an energy source, usually in the form of a carbohydrate such as glucose; c) vitamins and/or other organic compounds required at low concentrations; d) free fatty acids; and e) trace elements, where trace elements are defined as inorganic compounds or naturally occurring elements that are typically required at very low concentrations, usually in the micromolar range. The defined medium may also optionally be supplemented with one or more components from any of the following categories: a) one or more mitogenic agents; b) salts and buffers as, for example, calcium, magnesium, and phosphate; c) nucleosides and bases such as, for example, adenosine and thymidine, hypoxanthine; and d) protein and tissue hydrolysates.

As used herein, "conditioned media" refers to culture media, free of intact cells, in which ovarian cells have been grown. Ovarian cells grown in nutrient media may release factors which promote the continued survival, growth, and maintenance of pre-existing state of pre-differentiation of the ovarian mesothelial cells. Conditioned media may be used to reconstitute a cell pellet or added to cells already existing in culture plates. Conditioned media may also be used alone or to supplement nutrient media being used to feed ovarian cells.

"Standard incubation conditions" refers to the physicochemical conditions in an incubator designed for tissue culture in which cells are placed. Generally, the standard incubation conditions are about 37 degrees Celsius and about 5% $CO_2$ content with humidification. All tissue culture techniques and equipment should be performed under sterile conditions.

Ovarian mesothelial cell clusters", "ovarian mesothelial cell spheres", and "ovarian cell clusters" are used interchangeably throughout and refers to a mass of a plurality of ovarian mesothelial cells. Ovarian mesothelial cell clusters can form a three-dimensional structure resembling roughly a sphere.

A "grafting recombinant", as used herein, refers to the combined unit of ovarian mesothelial cell clusters placed with mesenchymal tissue. Mesenchymal tissue can be of ovarian or non-ovarian origin. Mesenchymal tissue can be from a species heterologous to the graft recipient. Mesenchymal tissue can also be from a species heterologous to the source of ovarian mesothelial cells. Grafting recombinants can be incubated on substrate, preferably a soft, biological substrate (e.g. agar) for a period ranging from about 1 hour to 96 hours, more preferably between about 6 hours to 48 hours, and even more preferably, overnight with an incubation period of about 24 hours.

"Serum", as used herein, refers to the fluid phase of mammalian blood that remains after blood is allowed to clot.

"Serum biomolecules", as used herein, refers to biological compositions found in serum. Examples include, but are not limited to, albumin, $\alpha 1$-globulin, $\alpha 2$-globulin, $\beta$-globulin, and $\gamma$-globulin. Serum biomolecules can include biological compositions, whole or partial, that are either naturally found in serum or derived from processing and handling of serum.

The terms "mammals" or "mammalian" refer to warm blooded vertebrates which include but are not limited to humans, mice, rats, rabbits, simians, sport animals, and pets.

Isolation and Maintenance of Human Ovarian Mesothelial Cells

Ovarian mesothelial cells of this invention are isolated from human fetal ovarian tissue. The age of the fetus is between about week 1 and about week 40, preferably between about week 8 and about week 30, and even more preferably between about week 17 and about week 25. The ovarian tissue can be identified by gross anatomy, outward appearance, and location within the fetus. Several features of gross anatomy and appearance distinguishing a ovary are its crescent shape and location in the abdominal cavity. The ovary may also be associated with fallopian tubes. Once identified, fetal ovarian tissue is first cleaned by washing with basal nutrient medium and then microdissected. The purposes of microdissection are to remove adjacent tissue to the ovary and to divide the solid ovarian tissue mass into smaller parts of the whole tissue mass so that the basal nutrient media has greater access to ovarian cells within the tissue pieces and/or to separate ovarian cells from ovarian tissue mass. Non-limiting examples of microdissection include devices that render mechanical shearing forces (i.e. homogenizer, mortar and pestle, blender, etc.), devices that render cuts or tears (i.e. scalpel, syringes, forceps, etc.), or ultrasonic devices. Alternatively, another method of microdissecting fetal ovarian tissue is the use of enzyme treatment. Various enzyme treatments used to microdissect tissue are well known in the art. One method includes the use of collagenase-dispase to digest partially sheared ovarian tissue in a buffered medium that will sustain viability of cells isolated from the ovarian tissue. The amount of enzyme will depend on the age of the fetus and how large the ovarian tissue is. In one embodiment, enzyme treatment with collagenase-dispase may lower the overall cell yield. Accordingly, the amount of enzyme used would be reduced or not used at all. In other embodiments, enzyme treatment may increase overall cell yield. Accordingly, enzyme treatment may be used alone or in combination with microdissection methods. A wide variety of basal cell-sustaining media that can be used to keep the pH of the liquid in a range that promotes survival of ovarian mesothelial cells and to provide additional volume of liquid within which the enzymatic digestion can occur. Non-limiting examples include F12/DMEM, Ham's F10 (Sigma), CMRL-1066, Minimal essential medium (MEM, Sigma), RPMI-1640 (Sigma), Dulbecco's Modified Eagle's Medium (DMEM, Sigma), and Iscove's Modified Eagle's Medium (IMEM). In addition, any of the basal nutrient media described in Ham and Wallace (1979) *Meth. Enz.*, 58:44, Barnes and Sato (1980) *Anal. Biochem.*, 102:255, or Mather, J. P. and Roberts, P. E. (1998) "Introduction to Cell and Tissue Culture", Plenum Press, New York can also be used.

Small pieces of ovarian tissue are placed in a basal cell-sustaining media. A variety of basal cell-sustaining media is available for use. Examples include, but are not limited to, Ham's F12 medium, RPMI-1640, and CMRL-1066. For more optimal conditions to promote ovarian mesothelial cell survival and growth, a variety of nutrients may be added to supplement the basal media. Examples include, but are not limited to, insulin, transferrin, epidermal growth factor, $\alpha$-tocopheral, recombinant human heregulin, aprotinin, fetal bovine serum, and bovine serum albumin. In a preferred embodiment, the following amounts of nutrients are used to promote ovarian mesothelial cell survival and growth: at least about 10 ng/ml insulin and not more than about 1 mg/ml insulin, more preferably about 10 $\mu$g/ml insulin; at least about 1 $\mu$g/ml transferrin and not more than about 100 $\mu$g/ml transferrin, more preferably about 10 $\mu$g/ml transferrin; at least about 1 ng/ml epidermal growth factor and not more than about 1000 ng/ml epidermal growth factor, more preferably about 50 ng/ml epidermal growth factor; at least about 0.1 $\mu$g/ml $\alpha$-tocopherol and not more than about 1 mg/ml $\alpha$-tocopherol, more preferably about 5 $\mu$g/ml $\alpha$-tocopherol; at least about 0.1 nM recombinant human heregulin and not more than about 100 nM recombinant human heregulin, more preferably about 10 nM recombinant human heregulin,; at least about 1 $\mu$g/ml aprotinin and not more than about 100 $\mu$g/ml aprotinin, more preferably about 5 $\mu$g/ml aprotinin; at least about 0.1% bovine serum albumin (BSA) and not more than about 50% BSA, more preferably about 2% BSA.

Ovarian mesothelial cells migrate out the ovarian tissue into the media in which the ovarian tissue is placed. In one embodiment, the ovarian mesothelial cells migrate out of the ovarian tissue into the media in cluster form. In another embodiment, the ovarian mesothelial cells migrate out of the ovarian tissue into the media in the form of single cells. In another embodiment, the ovarian mesothelial cells that migrate out of the ovarian tissue are no longer imbedded in the ovarian tissue but are loosely associated with the tissue. The ovarian mesothelial cells may be grown on different substrates. Non-limiting examples of substrates that may be used include fibronectin, laminin, collagen, polylysine, nitrocellulose, nylon, and polytetrafluoroethylene. In one embodiment, ovarian mesothelial cells are grown on laminin-coated tissue culture plates in the preferred nutrient media described above. In a preferred embodiment, ovarian mesothelial cells are grown in laminin-coated tissue flasks in the preferred nutrient media described above. The size of the tissue culture plates or flasks are proportional to the amount of ovarian tissue being placed within the plates or flasks. A skilled artisan may determine the correct size of the flask or plate by a stepwise increment of ovarian tissue placed within the tissue culture plates or flasks. When the ovarian tissue is first placed within the plates or flasks, the media is generally clear in overall turbidity. As ovarian mesothelial cells migrate out and away from the ovary tissue pieces, the media will become more opaque and more turbid. At the point where the media is highly turbid because of the increasing amount of ovarian mesothelial cells migrating from the ovarian tissue or because of ovarian mesothelial cell growth, more nutrient media is placed in the plates or flasks to replenish the nutrients consumed by the ovarian cells. In the alternative, when the media becomes turbid with increasing amounts of ovarian mesothelial cells, a small amount of cells may be removed from the culture plates or flasks and checked for cell viability, for example, with trypan blue staining. Plates or flasks that have been overrun with too many cells will begin to show decreased cell viability. The skilled artisan may then transfer the contents of the plates or flasks to other plate or flasks of a larger size (e.g. greater cubic volume) to accommodate the increasing amount of cells. In one embodiment, the entire content of the plate or flask is transferred to another plate or flask of a larger cubic volume. In another embodiment, the ovarian cell suspension is split into several parts, each part is placed in a separate plate or flask and then nutrient media is added to the ovarian cells (also known as "subculturing"). Ovarian mesothelial cells form cell clusters when cultured in the preferred nutrient media in laminin-coated flasks. The culturing combination of tissue culture flasks and laminin coating allows for separation of mesenchymal cells and ovarian mesothelial cell clusters. Mesenchymal cells migrate throughout the volume of the media while ovarian mesothelial cell clusters associate in close physical proximity with the ovarian tissue. In another embodiment, ovarian mesothelial cells are grown in the preferred nutrient media described above in laminin-coated tissue culture plates. Ovarian mesothelial cells form monolayers in this embodiment.

Ovarian mesothelial cells cultured in the preferred nutrient media in laminin-coated tissue culture flasks will form cell clusters that are in close physical proximity with ovarian tissue. When enrichment of the ovarian mesothelial cells is desired, one method that may be employed is enzymatic treatment to dissociate ovarian mesothelial cells followed by isolation of the ovarian mesothelial cell clusters. Examples of enzymes that can be used in enzymatic treatment include but are not limited to collagenase-dispase and trypsin. In one embodiment, collagenase-dispase is used to dissociate ovarian mesothelial cell clusters from culture flask walls and from ovary tissue, preferably at least about 10% (w/v) is used, more preferably at least about 1% of collagenase-dispase is used, most preferably at least about 0.1% of collagenase-dispase is used. Ovarian mesothelial cell clusters are isolated by using a density gradient. Compounds that can be used to achieve cell separation include, but are not limited to, serum (i.e. bovine serum albumin or BSA), ovalbumin, nonionic synthetic polymers of sucrose (i.e. Ficoll™), colloidal polyvinylpyrrolidone-coated silica (i.e. Percoll™), polyvinylpyrrolidone or PVP, and methylcellulose. In a preferred embodiment, density gradients that are capable of neutralizing collagenase-dispase are used. One example of such a density gradient is BSA. The amount of BSA used is about 50% volume-to-volume ratio with the preferred nutrient media, more preferably about 25%, more preferably about 10%, more preferably at least about 0.1%, and most preferably about 1% to 3%. In some cases, one density gradient is sufficient to enrich a population of ovarian mesothelial cells. In other cases, more than one application of a density gradient will be needed. The desired product is a population of substantially pure ovarian mesothelial cell clusters.

In one embodiment, a substantially pure population of ovarian mesothelial cell clusters is isolated by spinning ovarian cells through a density gradient like BSA at a spinning rate sufficient to pellet the ovarian mesothelial cell clusters and leave single mesenchymal cells in the supernatant. The cell pellet with ovarian mesothelial cells is resuspended in a nutrient media sufficient to sustain life of the ovarian mesothelial cells and placed in a tissue culture flask which is coated with a biological substrate, for example laminin. The entirety of the volume of resuspended ovarian mesothelial cells may be placed in one flask. In an alternative, if the resuspended ovarian mesothelial cells is highly enriched and has a high density of ovarian mesothelial cells, then the volume of resuspended ovarian mesothelial cells may be split into several different flasks to which the preferred nutrient media is added. In a preferred embodiment, the following amounts of nutrients are used to promote the survival and growth of the substantially pure population of ovarian mesothelial cells: at least about 10 ng/ml insulin and not more than about 1 mg/ml insulin, more preferably about 10 µg/ml insulin; at least about 1 µg/ml transferrin and not more than about 100 µg/ml transferrin, more preferably about 10 µg/ml transferrin; at least about 1 ng/ml epidermal growth factor and not more than about 1000 ng/ml epidermal growth factor, more preferably about 50 ng/ml epidermal growth factor; at least about 0.1 µg/ml α-tocopherol and not more than about 1 mg/ml α-tocopherol, more preferably about 5 µg/ml α-tocopherol; at least about 0.1 nM recombinant human heregulin and not more than about 100 nM recombinant human heregulin, more preferably about 10 nM recombinant human heregulin; at least about 1 µg/ml aprotinin and not more than about 100 µg/ml aprotinin, more preferably about 5 µg/ml aprotinin; at least about 0.1% bovine serum albumin (BSA) by volume and not more than about 50% BSA, more preferably about 0.5% BSA.

The frequency of feeding ovarian mesothelial cells may be once a day or every other day. In one embodiment, ovarian mesothelial cells may be fed by replacing the entirety of the old nutrient media with new nutrient media. In another embodiment, ovarian mesothelial cells may be fed with conditioned media in which these cells were grown. Because the claimed ovarian mesothelial cells are unique to this invention and will secrete factors specific to these cells, the conditioned media derived from the ovarian mesothelial cells are also unique. In this invention, ovarian mesothelial cells form clusters when grown in the preferred nutrient media, defined above, in laminin-coated tissue culture flasks. When the substrate is laminin-coated tissue culture plates, ovarian mesothelial cells form an attached stromal monolayer. In a preferred embodiment of the invention, cell to cell contact of ovarian mesothelial cells to each other is maintained throughout the culturing of ovarian mesothelial cells to promote a higher proliferation rate. Addition of conditioned media may also promote better growth of the ovarian mesothelial cells. A skilled artisan can determine if the addition of conditioned media is advantageous to the growth of ovarian mesothelial cells by supplementing the nutrient media stepwise with an increasing amount of conditioned media. Cell growth can be determined by counting the number of cells per volume of media before and after the addition of conditioned media. Alternatively, cell viability (e.g. trypan blue) can be used to assess if addition of conditioned media to the culturing condition is advantageous to the growth of the ovarian mesothelial cells. A frequency of feeding that is preferable for promoting the survival and growth of ovarian mesothelial cells is once a week, even more preferably is twice a week, and most preferably every other day. The ovarian mesothelial cells of this invention can be passaged multiple times without inducing differentiation of these ovarian mesothelial cells into terminally differentiated ovarian surface epithelial cells and granulosa cells.

Characterization of Ovarian Mesothelial Cells

The population of ovarian mesothelial cells of this invention isolated in the manner disclosed herein have several defining characteristics. First, the ovarian mesothelial cells are at a stage that can be described as "pre-determined ovarian". Of the mesothelial progenitor cells, some are predetermined to become ovarian mesothelial cells. It is at this stage of development that the population of ovarian mesothelial cells claimed herein resides. The ovarian mesothelial cells of this invention have the capacity to become either ovarian surface epithelial cells and granulosa cells but have not begun to differentiate into either cell type.

Identification of ovarian mesothelial cells may be accomplished by morphology or specific markers or a combination of both techniques. Granulosa cells line form the wall of an ovarian follicle. Morphology of granulosa cells is a cuboidal shape. Markers that can be used to detect ovarian mesothelial cells include but are not limited to cytokeratin (CK) 1, 5, 6, 7, 8, 10, 11, 13, 15, 16, 18, and 19, anti-ovary monoclonal antibody 5C8, and vimentin on ovarian mesothelial cell surfaces. Examples of antibodies specific for CK and vimentin that may be used include, but are not limited to: anti-cytokeratin (CK) antibodies clone 4.62, clone 8.12, clone 8.13 from Sigma Chemical Co. and anti-vimentin antibodies clone 13.2 from Sigma Chemical Co. Anti-CK antibodies and anti-vimentin antibodies can be used in either direct or indirect staining of MTE cells in immunohistochemistry or by flow cytometry. Markers to detect ovarian mesothelial cells can be used in direct and indirect immunofluorescence, immunohistochemistry, and flow cytometry.

Ovarian mesothelial cells of this invention are maintained at their preexisting pre-differentiation state in basal nutrient media. Basal cell-sustaining media or the preferred nutrient media disclosed herein or conditioned media may be used to culture the ovarian mesothelial cells in vitro. Different types of substrate on tissue culture plates can be used to obtain either clusters or monolayers of ovarian mesothelial cells. The use of laminin-coated flasks in conjunction with the preferred nutrient media disclosed herein results in clusters of ovarian mesothelial cells whereas the use of laminin-coated plates in conjunction with the preferred nutrient media disclosed herein results in monolayers of ovarian mesothelial cells. Ovarian mesothelial cells of this invention may be cultured in serum-free nutrient media or serum-containing nutrient media. As is well-known to those of ordinary skill in the art, serum is commonly added to nutrient media to further enhance cell growth. Serum contains many serum biomolecules, however, the ovarian mesothelial cells of this invention may be grown in the absence of a plurality of these serum biomolecules. Cell growth of ovarian mesothelial cells may be enhanced by the addition of one or more proteins found in serum, for example, bovine serum albumin (or BSA).

Ovarian mesothelial cells of this invention have the capacity to be passaged multiple times in the preferred basal nutrient media disclosed herein. Multipotency is retained during each passage and at any point after each passage, ovarian mesothelial cells of this invention can differentiate into ovarian surface epithelial cells and granulosa cells. In addition, at any point after each passage, ovarian mesothelial cells may be used as an immunogen, for cell therapy, for bioassays, to establish a human ovarian model, or for drug discovery and/or development as disclosed herein.

Another characteristic of the ovarian mesothelial cells of this invention is the capacity to differentiate into ovarian surface epithelial cells and granulosa cells upon transplantation under kidney capsule of a recipient mammal. Prior to transplantation, ovarian mesothelial cells have the capacity to differentiate into granulosa cells or ovary surface epithelial cells. As disclosed herein, ovarian mesothelial cells can be grown either in ovarian mesothelial cell clusters or in monolayers and then combined with mesenchymal tissue and placed under a kidney capsule of a recipient mammal. Preferably, human ovarian mesothelial cell clusters are combined with rat urogenital mesenchymal tissue and placed under the kidney capsule of a recipient mammal. A portion of the transplant may be removed for analysis using the markers, morphology, or a combination thereof to identify the ovarian cells.

Uses of Ovarian Mesothelial Cells

Uses as an Immunogen

One use for ovarian mesothelial cells is as an immunogen. Ovarian mesothelial cells isolated and cultured with the methods disclosed herein can be used as an immunogen that is administered to a heterologous recipient. Administration of ovarian mesothelial cells as an immunogen can be accomplished by several methods. Methods of administrating ovarian mesothelial cells as immunogens to a heterologous recipient include but are not limited to: immunization, administration to a membrane by direct contact such as swabbing or scratch apparatus, administration to mucous membrane by aerosol, and oral administration. As is well-known in the art, immunization can be either passive or active immunization. Methods of immunization can occur via different routes which include but are not limited to intraperitoneal injection, intradermal injection, local injection. Subjects of immunization may include mammals such as mice. The route and schedule of immunization are generally in keeping with established and conventional techniques for antibody stimulation and production, for example, injecting immunogen in foot pads of mice once a week for several weeks. While mice are employed in this embodiment, any mammalian subject including humans or antibody producing cells therefrom can be manipulated according to the processes of this invention to serve as the basis for production of mammalian hybridoma cell lines. Typically, mice are inoculated with an immunogenic amount of the ovarian mesothelial cells and then boosted with similar amounts of the immunogen. In an alternative, cells grown on non-biological membrane matrix, are surgically implanted intraperitoneally into the host mammal. Lymphoid cells, preferably spleen lymphoid cells from the mice, are collected a few days after the final boost and a cell suspension is prepared therefrom for use in the fusion.

Hybridomas are prepared from the lymphocytes and immortalized myeloma cells using the general somatic cell hybridization technique of Kohler, B. and Milstein, C. (1975) *Nature* 256:495–497 as modified by Buck, D. W., et al., (1982) *In Vitro,* 18:377–381. Available myeloma lines, including but not limited to X63-Ag8.653 and those from the Salk Institute, Cell Distribution Center, San Diego, Calif., USA, may be used in the hybridization. The technique involves fusing the myeloma cells and lymphoid cells using a fusogen such as polyethylene glycol, or by electrical means well known to those skilled in the art. After the fusion, the cells are separated from the fusion medium and grown in a selective growth medium, such as HAT medium, to eliminate unhybridized parent cells. Any of the media described herein can be used for culturing hybridomas that secrete monoclonal antibodies. As another alternative to the cell fusion technique, EBV immortalized B cells are used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen.

In this manner, a panel of novel antibodies to cell surface antigen specific to a stage of ovarian mesothelial cells can be generated using the ovarian mesothelial cells of this invention as an immunogen. Once monoclonal antibodies to cell surface antigens on ovarian mesothelial cells are made by the method disclosed herein, the antibodies can be used for several uses. The antibodies may be sequenced and cloned for purposes of generating recombinant antibodies or humanized antibodies. Other uses of ovarian mesothelial cell-specific antibodies include, but are not limited to, biological testing and purification (i.e. isolation of ovarian mesothelial cells, for example by flow cytometry or antibody panning), therapeutic uses (i.e. promoting or arresting cell growth by binding of antibody to target cell or promoting or arresting growth of a cell mass by binding of antibody to target cell), biological markers (i.e. identification of other ovarian or non-ovarian cells), clinical diagnosis (i.e. identification of cancerous ovarian cells in tissue samples).

Another use as an immunogen is to modulate overall immune response in a heterologous recipient. As is well-documented in the art, foreign substances such as cells or organs introduced into a heterologous recipient may induce a variety of immune responses. The immune responses can be in the form of rejection (e.g. in organ transplantation), T cell activation (e.g. cross-priming), anergy, or tolerance. The overall immune response can be systemic or localized. In the case where a localized immune response is desired, for example in the gonadal region, an immunogen such as ovarian mesothelial cells is introduced into the gonadal region in an effective amount. Effective amount can be determined in a stepwise fashion in which increasing amounts of ovarian mesothelial cells are introduced into a heterologous recipient and the subsequent immune response is monitored. Overall immune response (e.g. antibody production, cytokine production, T cell proliferation, anergy, tolerance, etc.) may be monitored by a number of methods including but not limited to ELISA, proliferation assays, flow cytometry with cell surface markers, and immunohistochemistry.

Use of Ovarian Mesothelial Cells for Drug Discovery

Another use of ovarian mesothelial cells is related to drug discovery. Since the multipotent pre-determined ovarian mesothelial cell population has not been isolated and cultured in the disclosed manner, the ovarian mesothelial cell population may secrete proteins that have not been heretofore discovered or characterized. Therefore, proteins secreted by ovarian mesothelial cells may be used as targets for drug development. In one embodiment, drugs can be made to target specific proteins on ovarian mesothelial cells in vivo. Binding of the drug may promote differentiation of the ovarian mesothelial cells into ovarian surface epithelial cells or granulosa cells. This approach may be useful when ovarian surface epithelial cell or granulosa cell neogenesis is desired, for example to replace damaged cells after cancer therapy (e.g. chemotherapy, radiation therapy, etc.). In another embodiment, drug specific for regulatory proteins of ovarian mesothelial cells may be used to arrest growth of a particular type of cell, for example in cases of cancer (i.e. ovarian cancer, uterine cancer, etc.).

Uses of Ovarian Mesothelial Cells for Cell Therapy

In another use, ovarian mesothelial cell lines are used for cell therapy. Transplantation of ovarian mesothelial cells is one such example of cell therapy. In cases where different types of ovarian cells (i.e. OSE cells or granulosa cells) are desired, transplantation of ovarian mesothelial cells may be employed because the ovarian mesothelial cells of this invention are multipotent and can differentiate into ovarian surface epithelial cells and granulosa cells. To practice this use, ovarian mesothelial cells are isolated and cultured in basal nutrient, nutrient-defined media using the methods disclosed. Ovarian mesothelial cells are grown on laminin-coated tissue culture flasks to obtain ovarian mesothelial cell clusters. Ovarian mesothelial cell clusters are grown under standard incubation conditions for about half a day to at least about 1 cell cycle passage, more preferably for at least about 2 cell cycle passage, most preferably at least about 3 cell cycle passages. Ovarian mesothelial cell aggregates can then be administered to a recipient and allowed to differentiate. In an alternative, ovarian mesothelial cell aggregates can be used as cellular carriers of gene therapy wherein ovarian mesothelial cells are transfected with one or more genes and enclosed in a delivery device and then administered to a recipient. In another embodiment, ovarian mesothelial cell aggregates are placed under a kidney capsule and allowed to differentiate into OSE or granulosa cells. In another embodiment, ovarian mesothelial cell aggregates are used in a device which contains cells and limits access from other cells (i.e. Theracyte®) to limit immune system responses.

Uses of Ovarian Mesothelial Cells to Make Human Tissue Models

Another use for ovarian mesothelial cells is to generate human ovary tissue models in non-human mammals. A human ovary tissue models can be employed to study multiple facets of ovary development or ovary carcinogenesis, an important area of ovarian cancer research. Ovarian mesothelial cell spheres are placed on top of mesenchymal tissue to form grafting recombinants. To form grafting recombinants, about 1 to 15 ovarian mesothelial cell spheres, more preferably about 5 to 8 spheres, are placed on top of mesenchymal tissue. The mesenchymal tissue may be either ovarian or non-ovarian tissue and may be derived from a different species from which ovarian mesothelial cells are isolated. In a working example, human ovarian mesothelial cells are placed on top of rat mesenchymal urogenital tissue to form a graft recombinant. A skilled artisan may determine the optimal combination for human ovarian mesothelial cell growth in a stepwise fashion, by first isolating human ovarian mesothelial cells using the methods disclosed herein and then combining with mesenchymal tissue from different organs. In some embodiments, a different species, e.g. rat, is used as a source for mesenchymal tissue in combination with human ovarian mesothelial cells. The use of heterologous species allows human-specific markers to be used to determine the identity of differentiated human ovarian cells. The likelihood of false positives is reduced if rat mesenchymal tissue is used. Likewise, the use of urogenital mesenchymal tissue over ovarian mesenchymal tissue reduces the likelihood of false positives in identifying differentiated ovarian cells. In a preferred embodiment, about 1 to 12 ovarian mesothelial cell spheres, even more preferably about 5 to 8 ovarian mesothelial cell spheres, are placed on top of rat urogenital mesenchymal cells. Preferably, about $1 \times 10^4$ to about $5 \times 10^6$ mesenchymal cells are used. Even more preferably, about $2 \times 10^5$ to about $5 \times 10^5$ mesenchymal cells are used. A graft recombinant comprising ovarian mesothelial cell spheres placed on mesenchymal tissue is then placed under the kidney capsule of a recipient mammal. Possible recipient mammals include but are not limited to mice and rats. Typically in graft situations, donor tissue is vulnerable to attack by the recipient's immune system. To alleviate graft rejection, several techniques may be used. One method is to irradiate the recipient with a sub-lethal dose of radiation to destroy immune cells that may attack the graft. Another method is to give the recipient cyclosporin or other T cell immunosuppressive drugs. With the use of mice as recipient mammals, a wider variety of methods are possible for alleviating graft rejection. One such method is the use of an immunodeficient mouse (nude or severe combined immunodeficiency or SCID). In a working example, human ovarian mesothelial cell spheres are placed on rat urogenital mesenchymal tissue and placed under the kidney capsule of an immunodeficient mouse. The graft recombinant remains in the recipient for about 1 to about 52 weeks, preferably about 5 to about 40 weeks, and even more preferably about 6 to about 8 weeks before the grafts are harvested and analyzed for ovarian mesothelial cell differentiation. In some cases, a small portion of the graft is needed for analysis. Markers specific for the ovarian surface epithelial cell and granulosa cells include, but are not limited to, cytokeratins 1, 5, 6, 7, 8, 10, 11, 13, 15, 16, 18, and 19, follicle stimulating hormone (FSH) receptor, luteinizing hormone (LH) receptor, and aromatase) may be utilized to confirm the identity of the differentiated ovarian mesothelial cells. Non-limiting methods of confirming markers are immunohistochemical analysis, immunofluorescence, and flow cytometry. Another method of identifying the differentiated ovarian mesothelial cells and assessing the success of the transplantation is to stain for the presence of 17β-hydroxysteroid dehydrogenase (17β-HSDH) in ovarian surface epithelial cells (OSE) or delta 5-3β-hydroxysteroid dehydrogenase presence in granulosa cells. These markers can be used separately or in combination with each other. In addition, a combination of one or more of these markers may be used in combination with cell morphology to determine the efficacy of the transplantation.

In one embodiment, human ovarian model can be generated in a SCID (severe combined immunodeficiency) mouse. The human ovarian model can be made by utilizing the human ovarian mesothelial cells isolated and cultured with methods disclosed herein and using the human ovarian mesothelial cells to make graft recombinants. Graft recombinants are then placed under the kidney capsule of mice. After about 1 to 10 weeks, preferably about 6 to 8 weeks after implantation under the kidney capsule, the graft or portion thereof is harvested and analyzed by immunohistochemistry. Markers specific to ovarian surface epithelial cells and granulosa cells include, but are not limited to, cytokeratin (i.e. CK 1, 5, 6, 7, 8, 10, 11, 13, 15, 16, 18, and 19), follicle stimulating hormone (FSH) receptor, luteinizing hormone (LH) receptor, and aromatase. Markers specific to ovarian surface epithelial cells and granulosa cells are used to analyze the efficacy of the tissue model system. Alternatively, markers specific for differentiated ovarian mesothelial cells are used. Non-limiting examples of these markers are: cytokeratin-19, vimentin, and monoclonal antibody 5C8. Yet another way to assess the results of ovarian mesothelial cell differentiation is by morphology. Ovarian surface epithelial cells have the appearance of flat or columnar epithelial cells.

Uses of Ovarian Mesothelial Cells in Bioassays

The ovarian mesothelial cells disclosed herein can be used in various bioassays. In one use, the ovarian mesothelial cells are used to determine which biological factors are required for differentiation. By using the ovarian mesothelial cells in a stepwise fashion in combination with different biological compounds (such as hormones, specific growth factors, etc.), one or more specific biological compounds can be found to induce differentiation of ovarian mesothelial cells to OSE cells. Employing the same stepwise combinations, one or more specific biological compound can be found to induce differentiation of ovarian mesothelial cells to granulosa cells. Other uses in a bioassay for ovarian mesothelial cells are differential display (i.e. mRNA differential display) and protein-protein interactions using secreted proteins from ovarian mesothelial cells. Protein-protein interactions can be determined with techniques such as yeast two-hybrid system. Proteins from ovarian mesothelial cells can be used to identify other unknown proteins or other cell types that interact with ovarian mesothelial cells. These unknown proteins may be one or more of the following: growth factors, hormones, enzymes, transcription factors, translational factors, and tumor suppressors. Bioassays involving ovarian mesothelial cells and the protein-protein interaction these cells form and the effects of protein-protein or even cell-cell contact may be used to determine how surrounding tissue, such as mesenchymal tissue, contributes to ovarian mesothelial cell differentiation.

EXAMPLES

Example 1

Isolation and Culturing of Ovarian Mesothelial Cells

Human fetal ovaries of gestational age between 17 to 25 weeks were obtained from Advanced Bioscience Research at Alameda county, Calif. Ovaries were procured and shipped to the lab in tissue culture medium under wet ice bath. Immediately upon arrival, the ovaries were cleaned of excess connective tissues, carefully separated from fallopian tube, and washed five times with fresh tissue culture medium.

The ovaries were minced with scissors or cut into small pieces (less than 1 mm thick) with a razor blade. The tissue pieces from each ovary were plated directly in a T75 flask freshly coated with laminin with 10 ml preferred nutrient medium as disclosed herein. Further dissociation of the ovaries with collagenase-dispase (0.5%) for 30 minutes at 37° C. could be done, but the procedure reduced the recovery of ovarian mesothelial cells. The cells were cultured in F12/DMEM supplemented with 10 μg/ml insulin, 10 μg/ml transferrin, 5 μg/ml α-tocopherol, 10 nM recombinant human heregulin β1, 50 ng/ml epidermal growth factor, 5 μg/ml aprotinin, and 2% BSA (by volume) at standard incubation conditions. Within a week, cells migrated from the explant and proliferated to form confluent cell cultures.

The cultures at this stage were consisted both ovarian mesothelial cells and mesenchymal cells. Mesenchymal cells migrated all over the flask, but ovarian mesothelial cells remained in close proximity to the tissue explants (FIG. 1A). To enrich the ovarian mesothelial cells, the cultures were detached from the culture flask by incubation with 0.1% collagenase-dispase for 30 minutes. The treatment dissociated the mesenchymal cells into single cells but left the ovarian mesothelial cells in the clusters. The ovarian mesothelial cells were then separated by centrifugation through BSA gradients (1%–3% BSA in F12/DMEM) for 5 minutes. The supernatant which contained mostly mesenchymal cells was aspirated and the cell pellet remaining contained mostly ovarian mesothelial cells. The ovarian mesothelial cells were resuspended in the culture medium and plated at a dilution factor of 1:5 (1 part cell suspension: 5 part total suspension volume). The culture medium was F12/DMEM supplemented with 10 µg/ml insulin, 10 µg/ml transferrin, 5 µg/ml α-tocopherol, 10 nM recombinant human heregulin β1, 50 ng/ml epidermal growth factor, 5 µg/ml aprotinin, and 0.5% BSA (by volume). The cells grew in suspension as clusters (FIG. 1B). The cells were propagated this way for about 4 to 5 passages. The cells grown in suspension culture were able to attach to the sides of the plate and grew as ovarian mesothelial cell monolayer (FIG. 1C) when serum was present in the culture medium or when the plates were coated with laminin. Monolayer cultures passage well when the ovarian mesothelial cells are kept in contact with each other.

Example 2

Characterization of Ovarian Mesothelial Cell Lines

Figure 3:
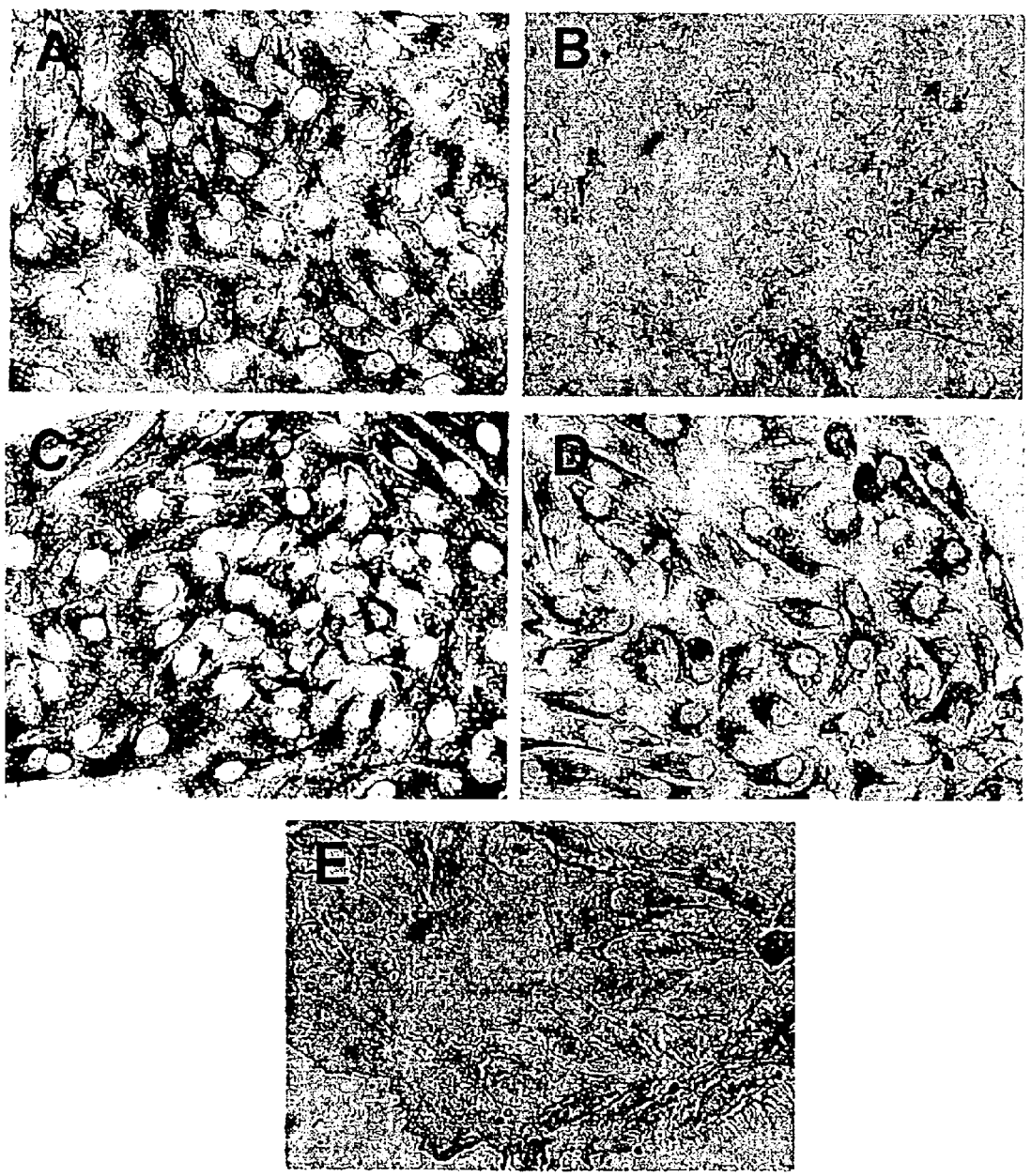
FIG. 3 shows the results of an immunoperoxidase staining of ovarian mesothelial cell clusters.

Ovarian mesothelial cells were harvested from suspension cultures. To directly stain the cells in cluster form, the cell clusters were embedded in optimal cutting temperature (OCT) compound and frozen on dry ice. Cryosections (5–10 µm thick) were cut of the OCT blocks, thaw-mounted onto coverslips, and fixed in 3% paraformaldehyde for 1 hour. A monolayer culture of ovarian mesothelial cells was prepared by plating the cell clusters from the suspension culture on chamber slides in the presence of 2% BSA. The monolayer cell cultures were fixed in situ with 3% paraformaldehyde for 1 hour. After the fixative was washed away with phosphate buffered saline (PBS), the cells were incubated in blocking buffer (5% goat serum and 0.1% Tween 20 in PBS) for 30 minutes, rinsed with PBS, then incubated in primary antibodies for 1 hour, rinsed with PBS, and then incubated with anti-mouse Ig-horseradish peroxidase for 1 hour. The markers and exemplary antibodies used to characterize ovarian mesothelial cells were CK 19 and anti-cytokeratin antibody clone 4.62 from Sigma Chemical Company (FIG. 3A), CK 13 and CK 16 and antibody clone 8.12 from Sigma Chemical Company (FIG. 3B), CK 10, CK 11, and CK 18 and antibody clone 8.13 from Sigma Chemical Company (FIG. 3C), vimentin and anti-vimentin monoclonal antibody clone 13.2 from Sigma Chemical Company (FIG. 3D), and anti-ovarian epithelial monoclonal antibody 5C8 (FIG. 3E). Monoclonal antibody 5C8 was made by using ovarian mesothelial cells as an immunogen.

Example 3

Figure 2:
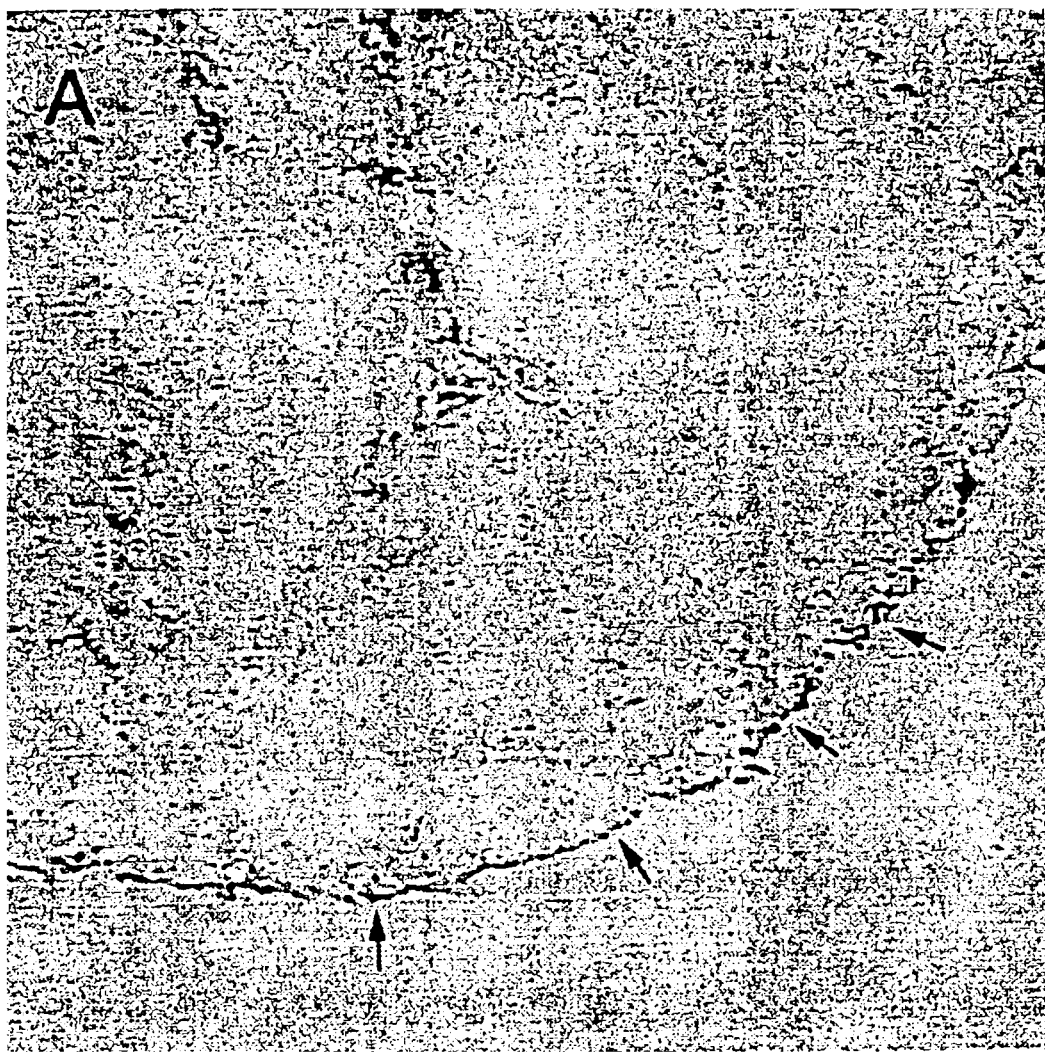
FIG. 2 shows the results of an immunohistochemical analysis wherein monoclonal antibody 5C8 specifically recognizes ovarian mesothelial cells in human fetal ovarian tissue.
Figure 2:

Method of Providing a Source of an Immunogen to Produce Monoclonal Antibodies Against Ovarian Mesothelial Cells Ovarian mesothelial cells were isolated and cultured as disclosed and then subsequently used as an immunogen to produce a panel of monoclonal antibodies against ovarian mesothelial cells. Mice were each immunized with one injection of about $1 \times 10^6$ cells of ovarian mesothelial cells per week. The immunization was localized into the foot pads of each mice. After 5 injections, the mice were bled to check the titer of ovarian mesothelial cells. When the titer of ovarian mesothelial cells rose above 1:1000 (ovarian cell-:total cells) in a mouse, the mouse was sacrificed and lymph nodes were harvested. Lymphocytes were prepared from the lymph nodes and fused to myeloma cell line to produce a hybridoma. Hybridomas were screened by flow cytometry (fluorescence-activated cell sorter or FACS) as well as by immunohistochemistry for monoclonal antibodies that specifically bound to ovarian mesothelial cells. Clonal hybridoma cell lines were obtained by repeated limiting dilutions. Hybridoma clone 5C8 was a monoclonal antibody clone that bound to ovarian mesothelial cells. FIG. 2 show the results in an immunohistochemical analysis where monoclonal antibody clone 5C8 specifically recognized ovarian mesothelial cells in fetal human ovaries.

Example 4

Use of Ovarian Mesothelial Cells to Generate a Human Ovarian Tissue Model

Figure 4:
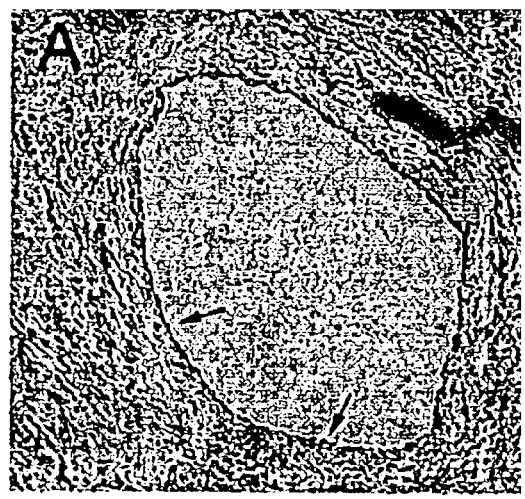
FIG. 4 shows the results of a tissue recombination experiment wherein human ovarian mesothelial cells were recombined with rat urogenital sinus mesenchymal tissue and transplanted into mice.
Figure 4:
Figure 4:

Tissue graft recombinants were made for the purposes of transplantation into a heterologous recipient either to generate a human ovarian tissue model in a heterologous recipient. To make tissue graft recombinants, ovarian mesothelial cells harvested from monolayer cultures after 3 passages was placed on top of rat urogenital sinus mesenchymal tissue. The graft recombinant was cultured on an agar plate for about 24 hours. Then the graft recombinant was implanted under the kidney capsule in nude mice. The implant was allowed to grow for about 2 months before the graft recombinant tissues were excised and analyzed by histology. The results showed that the ovarian mesothelial cells formed cystic structures (FIGS. 4A, 4B, and 4C). The epithelial cell lining of the ovarian surface epithelial cells was a thin sparse layer, loosely attached cells in some of the cysts (FIGS. 4A, 4B, and 4C).

Example 5

Use of Ovarian Surface Epithelial Cells in Bioassays

Figure 5:
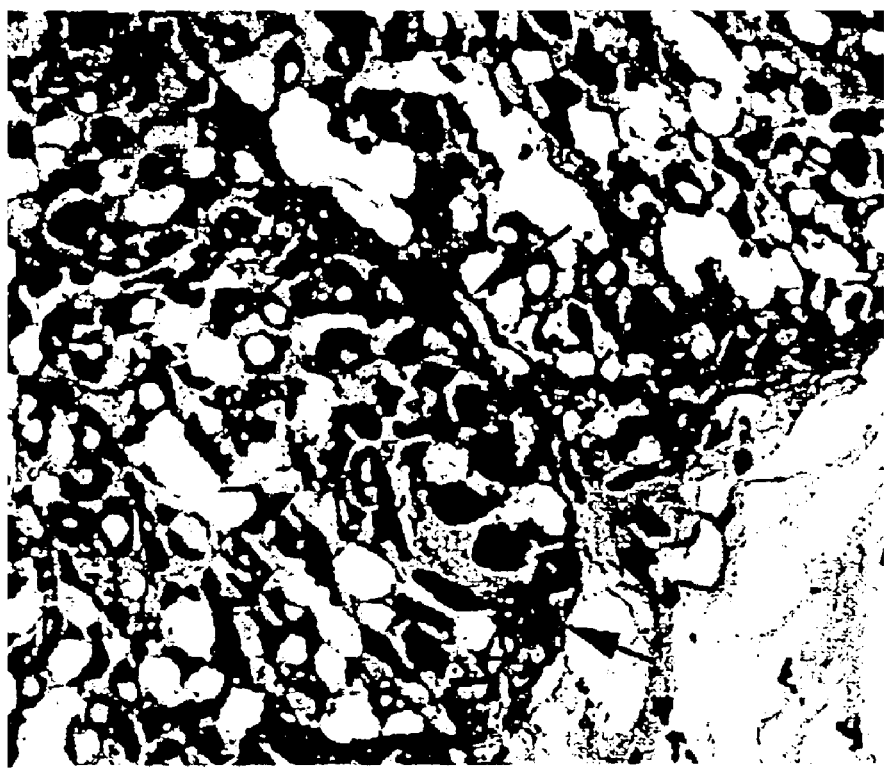
FIG. 5 show the results of immunohistochemical analysis wherein cancerous epithelial cell in ovarian cancer can be detected (brown, indicated by arrows) specifically by anti-ovary monoclonal antibody 5C8.
Figure 5:
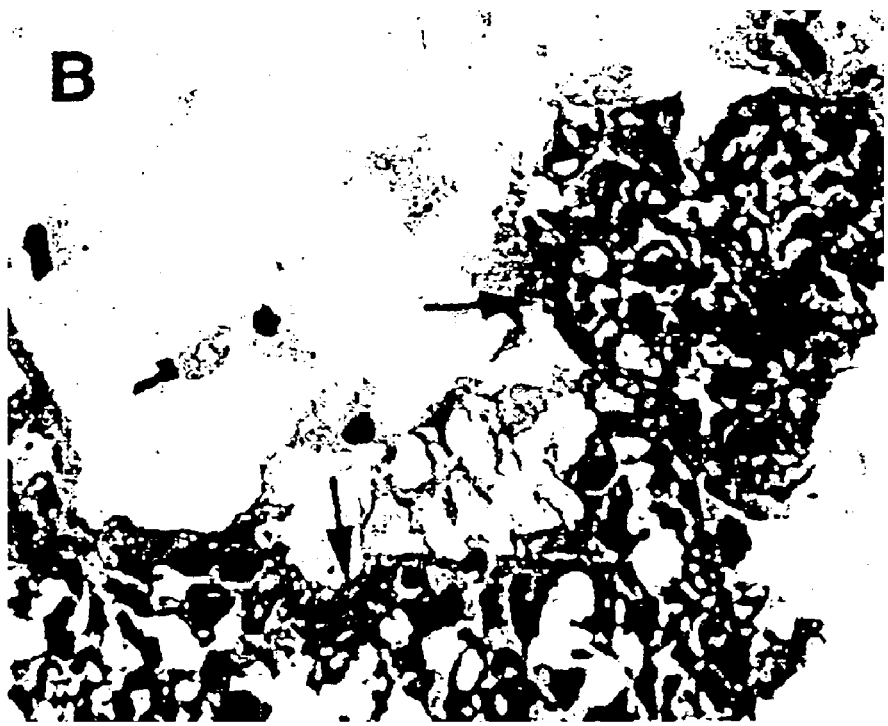

By using the ovarian mesothelial cells of this invention as immunogens, monoclonal antibodies specific to ovarian mesothelial cells such as clone 5C8 were generated. These antibodies were used to stain frozen sections of ovarian tissue from a female patient with ovarian cancer. Monoclonal antibody 5C8 showed strong staining of cancerous epithelial cells in a patient with ovarian cancer (FIG. 5). Thus the utility of monoclonal antibodies such as clone 5C8 can be extended to diagnostic purposes in a clinical setting.

What is claimed is:

1. A method of isolating a substantially pure population of ovarian mesothelial cells, comprising:
    (a) microdissecting a source of human fetal ovarian mesothelial cells;
    (b) placing the source of ovarian mesothelial cells in nutrient media under culture conditions sufficient to sustain life of said ovarian mesothelial cells and wherein the nutrient media contains nutrients consisting of insulin, transferrin, epidermal growth factor, α-tocopherol, recombinant human heregulin β1, bovine serum albumin, and aprotinin;

(c) maintaining suitable culture conditions sufficient to allow the migration of ovarian mesothelial cells from the source of ovarian mesothelial cells into the nutrient media;

(d) maintaining suitable culture conditions sufficient to allow ovarian mesothelial cells to form aggregate or monolayer formations; and (e) subculturing said aggregate or monolayer formations to obtain a substantially pure population of ovarian mesothelial cells.

2. A method of isolating a substantially pure population of ovarian mesothelial cells which have a pluripotent capacity to differentiate into ovary surface epithelial cells or granulosa cells, comprising the steps of:

(a) microdissecting a source of human fetal ovarian mesothelial cells;

(b) placing the source of ovarian mesothelial cells in nutrient media under culture conditions sufficient to sustain life of said ovarian mesothelial cells and wherein the nutrient media contains nutrients consisting of insulin, transferrin, epidermal growth factor, α-tocopherol, recombinant human heregulin β1, bovine serum albumin, and aprotinin;

(c) maintaining suitable culture conditions sufficient to allow the migration of ovarian mesothelial cells from the source of ovarian mesothelial cells into the nutrient media;

(d) maintaining suitable culture conditions sufficient to allow ovarian mesothelial cells to form aggregate or monolayer formations; and (e) subculturing said aggregate or monolayer formations to obtain an isolated, substantially pure population of ovarian mesothelial cells which have a pluripotent capacity to differentiate into ovary surface epithelial cells or granulosa cells.

* * * * *